(12) United States Patent
Andrews et al.

(10) Patent No.: US 6,830,895 B2
(45) Date of Patent: Dec. 14, 2004

(54) METHOD AND KIT FOR TYPING FELINE BLOOD

(75) Inventors: Gordon A. Andrews, Manhattan, KS (US); Joseph E. Smith, deceased, late of Manhattan, KS (US); by Katie L. Smith, legal representative, Manhattan, KS (US)

(73) Assignee: Kansas State University Research Foundation, Manhattan, KS (US)

( * ) Notice: Subject to any disclaimer, the term of this patent is extended or adjusted under 35 U.S.C. 154(b) by 110 days.

(21) Appl. No.: 09/916,465

(22) Filed: Jul. 26, 2001

(65) Prior Publication Data

US 2003/0092088 A1 May 15, 2003

(51) Int. Cl.$^7$ ................................................. G01N 33/53
(52) U.S. Cl. ........................ 435/7.32; 435/5; 435/7.21; 435/7.25; 435/7.92; 435/975; 436/164; 436/165; 436/579; 436/520; 436/524; 436/528; 436/538; 422/58; 422/72; 422/68.1; 422/61; 422/73; 422/99; 422/104
(58) Field of Search .................................. 496/164, 165, 496/514, 518, 519, 520, 524, 525, 528, 529, 534, 536, 538, 541, 805, 808, 824, 809; 435/5, 7.21, 7.32, 7.92, 7.25, 975; 422/58, 72, 68.1, 102, 61, 73, 99, 104

(56) References Cited

U.S. PATENT DOCUMENTS

| | | |
|---|---|---|
| 4,650,662 A | 3/1987 | Goldfinger et al. |
| 4,851,210 A | 7/1989 | Hewett |
| 5,145,774 A | 9/1992 | Tarnowski et al. |
| 5,302,512 A | 4/1994 | Pernelle |
| 5,776,711 A | 7/1998 | Vyas et al. |
| 5,863,802 A | 1/1999 | Yves et al. |
| 5,905,028 A | 5/1999 | Frame et al. |
| 6,024,883 A | 2/2000 | Jewell |
| 6,114,179 A | 9/2000 | Lapierre et al. |

OTHER PUBLICATIONS

Andrews et al. N–Glycolylneuraminic acid and N–acetylneuraminic acid define feline blood Group A and B Antigens, (Blood, 79(9) : 2485–2491, (May 1991)).*

Griot–Wenk et al. Biochemical characterization of the feline AB blood groups system, (Animal Genetics 24: 401–407 (1993).*

G. Andrews, P. Chavey, and J. Smith; Production and Characterization of Monoclonal Antibodies to Feline Blood Group A Erythrocytes. Vet. Pathol 33:5, 1996; Clinical Pathology; p. 577, #30.

J. Green, P. Chavey, and G. Andrews; Feline Blood Typing Using Monoclonal Antibodies, Meeting of the American Veterinary Hematology and Transfusion Medicine Society in Conjunction with the Annual Meeting of the American College of Veterinary Internal Medicine. Denver, Colorado, May, 2001. Abstract.

J. Green, P. Chavey, G. Andrews, and J. Smith; Characterization of Murine Monoclonal Antibodies to Feline Erythrocyte and B Antigens. Vet. Pathol. 36:5, 1999; ASVCP Meeting; p. 481, #4.

J. L. Green, P.S. Chavey, G. A. Andrews, and J. E. Smith; Production and Characterisation of Murine Monoclonal Antibodies to Feline Erythrocyte A and B Antigens; Comparative Haematology International (2000); pp. 30–37.

* cited by examiner

Primary Examiner—Long V. Le
Assistant Examiner—Jacob Cheu
(74) Attorney, Agent, or Firm—Patrick C. Woolley; Holly M. Amjad; Polsinelli Shalton Welte Suelthaus, PC

(57) ABSTRACT

The present invention relates to a kit for determining feline blood type, wherein the kit includes a mixture comprised of a first monoclonal antibody and a second monoclonal antibody, wherein both antibodies recognize feline blood group specific A antigens. The present invention also relates to a method for determining feline blood type, wherein the method utilizes two distinct monoclonal antibodies, which recognize feline blood group specific A antigens.

18 Claims, No Drawings

METHOD AND KIT FOR TYPING FELINE BLOOD

FIELD OF INVENTION

The present invention relates to a method and kit for typing feline blood. In particular, the present invention relates to a kit having a mixture of two monoclonal antibodies, which recognize feline specific A antigens on the feline erythrocytes.

BACKGROUND OF INVENTION

Knowledge of feline blood group antigens is important to determine so as to eliminate adverse reactions that can occur after blood transfusions. In particular, before a cat can be given a blood transfusion, it is necessary to determine the cat's blood type. If the wrong blood type is provided during a blood transfusion, a severe immune response may occur. Newborn kittens that nurse are also at risk because of naturally occurring anti-erythrocyte antibodies in the colostrum of some queens.

The consistent presence of naturally occurring antibodies to opposing blood types distinguishes cats from other major animal species in which this trait is absent or of minimal clinical significance. Of particular importance, most blood type B cats possess high titers of anti-A antibodies. These natural antibodies can result in severe haemolytic reactions to incompatible transfusions even on first administration. Neonatal isoerythrolysis and the related fading kitten syndrome are direct results of these potent anti-A antibodies. In contrast, only a small number of blood type A cats possess naturally occurring anti-B antibodies, and these are present in low titer. Blood type AB cats lack natural antibodies to either the A or B antigens.

Despite knowledge of the general organization and pattern of inheritance of the feline blood group system, it is still important to accurately blood type-subjects. This is especially true because in the rare AB blood type, the mode of inheritance is unknown. Of the three blood types, A, B, and AB, type A predominates in the more common Domestic shorthair/Domestic longhair (DSH/DLH) cats. Blood type B is much more likely to occur in certain breeds, particularly the Persian, Abyssinian, Birman, and related modern breeds, such as the Himalayan and British Shorthair. The AB blood type is by far the least common of the three and is characterized by the presence of both A and B antigens on the erythrocyte surface. Although blood type may be hypothesized with a fairly high degree of accuracy based on inherited characteristics, an individual's blood type can only be hypothesized if the blood type of the parents is known. Further, a statistical estimate can only be made if the parents are of different blood types. It is essential to type a subject's blood in order to determine the blood type. This is the only method to accurately determine the blood type.

Currently, feline anti-A antiserum harvested from type B cats is used as the typing reagent for detection of blood type A. To harvest the anti-A antiserum, a population of type B cats must be housed for a long time period. The cats must be periodically bled and the serum must be separated to use as the typing reagent. This process is problematic because the antibody titer, or concentration of antibody varies from one cat to another, introducing a variable that must be monitored between different batches of typing sera. Resultantly, these procedures can be costly. Also, the periodic bleeding of cats to harvest serum for blood typing purposes can be criticized or even prohibited by animal rights' groups and governmental agencies in many parts of the world.

With the availability of rapid card tests, the practice of blood typing cats is utilized more routinely by veterinary practitioners than in the past. Current blood-typing products use anti-A antiserum from blood type B cats to detect type A and wheat germ lectin (WGL) to detect type B. As mentioned, feline anti-A antiserum can be expensive and labor-intensive to obtain. In addition, variability in source and preparation can affect its specificity and sensitivity. Therefore, it is desired to develop more specific and easily produced reagents for use in feline blood-typing. It is further desired to have a method that does not require cats to be housed and periodically bled.

SUMMARY OF INVENTION

The present invention relates to a method and kit for determining feline blood type. The present invention also relates to at least one isolated feline antibody, which binds to one or more receptors on an antigen that characterizes feline type A blood. Both the kit and method include the use of two different monoclonal antibodies, which recognize feline blood group specific A-antigens. One of the antibodies will recognize glycolipid A antigen $(NeuGc)_2G_{D3}$. The other antibody will recognize a second glycolipid A antigen other than $(NeuGc)_2G_{D3}$. Any monoclonal antibody may be used, as long as feline blood type A can be accurately recognized and the erythrocytes are agglutinated. In particular, the invention is used to determine whether a blood sample contains feline glycolipid A antigens.

The kit is formed by selecting a substrate member, such as a card, which facilitates contact between a mixture of the first and second monoclonal antibody with a blood sample. Use of a card is preferred; however, any system or device that allows the antibody mixture to be contacted with a blood sample may be used. Alternative testing systems include the use of a test tube. Optionally, an agent which agglutinates with blood type B may be included in the kit. The antibodies can be used in any of a variety of concentrations, as long as the blood visibly agglutinates. It is also preferred that the antibodies be mixed with other constituents, which inhibit the degradation of proteins. It is further preferred if the moisture in the antibody mixture is eliminated so as to preserve the proteins. One way to preserve the proteins is to lyophilize the mixture.

The method includes collecting a blood sample from a feline subject and contacting an amount of the sample with the antibody mixture. The sample may also be contacted with an agent which agglutinates blood type B. The antibody and sample mixture is then observed to see if the blood agglutinates with the anti-A antibody, and, optionally, the anti-B agent.

Any antibody can be used with the present invention, as long as it has a receptor for binding with feline type A blood. A preferred monoclonal antibody will have a receptor site for glycolipid A antigen $(NeuGc)_2G_{D3}$. A preferred second monoclonal antibody will have a receptor site for glycolipid A antigen that is similar to $(NeuGc)G_{T3}$.

The present invention is advantageous because it provides for a quick and simple method for testing feline blood type. Additionally, the present method and kit alleviate the need to house a population of cats from which serum is harvested for use in blood typing. The present invention is also advantageous because it is more accurate than traditional testing methods. It is also more accurate than relying on known inheritance characteristics. Importantly, the present invention uses two separate monoclonal antibodies for determining blood type A.

DETAILED DESCRIPTION

The present invention relates to a method for typing feline blood samples and a kit associated therewith. Specifically, the method and kit use a mixture of first and second monoclonal antibodies, each of which recognizes feline blood group specific A antigens. As such, the kit and method can be used to accurately type feline blood. The present invention also relates to at least two monoclonal antibodies which can be used to identify feline blood type A. The antibodies included in the kit recognize feline A antigen $(NeuGc)_2G_{D3}$ and at least one other feline A antigen.

The kit is made by first forming monoclonal antibodies which recognize feline blood group specific A antigens. It is preferred to form a hybridoma cell line that produces the monoclonal antibodies. The monoclonal antibodies can be formed, however, according to any other procedure, which will result in the production of the desired antibodies. As such, the preferred method for forming the monoclonal antibodies and the hybridoma cell line is specifically disclosed in Example 1.

The preferred method starts with isolating blood from a type A cat. The erythrocytes are then separated from the serum followed by extracting the lipids from the erythrocyte membranes. Using thin layer chromotography it is possible to isolate the glycolipids from the remainder of the lipids. Liposomes, which incorporate the isolated erythrocyte membrane glycolipids, are next prepared. Mice or other host-organisms are then given an intraperitoneal injection of the liposome suspension. This will facilitate production of IgM antibodies. It is hypothesized, however, that other serum proteins having the same feline antigen A receptor site could be used. Lymphocytes are then harvested from the mice and fused with mouse myeloma cells. The resultant hybridoma culture cells are then screened for antibodies that recognize the feline specific A antigens. These cells, which produce the desired antibody, are further grown to expand the population.

It is preferred to have two hybridoma cell lines which produce two different monoclonal antibodies for detecting feline specific A antigens. Preferably, one antibody recognizes glycolipid A antigen $(NeuGc)_2G_{D3}$, the major glycolipid antigen of type A feline blood. It is additionally preferred if the other antibody recognizes a second glycolipid antigen, which may resemble $(NeuGc)G_{T3}$. By recognizing two different glycolipid antigens, the accuracy of the resultant kit, which includes two different antibodies, will be increased. The antibodies are specifically different because they have different antigen receptors. The inclusion of two different antibodies is important because the antibodies do not always recognize blood type A when used alone. Specifically, blood type AB has at least one A antigen, which can be either $(NeuGc)_2G_{D3}$, $(NeuGc)G_{T3}$, or an A antigen similar to $(NeuGc)G_{T3}$. The glycolipid detected by one of the antibodies is likely $(NeuGc)G_{T3}$, or another (NeuGc) containing ganglioside. Such gangliosides are found on type A red blooe cells. If two different antibodies directed at two different antigens are used correct identification of blood type AB is more likely to occur. It is necessary to use two different antibodies because blood type AB cats are heterogeneous. In order to accurately type such cats, two different antibodies that recognize a distinct A antigen are required.

The preferred monoclonal antibodies produced by the hybridoma cell lines are labeled 13G3 and 4E10 and are murine IgM antibodies. 4E10 corresponds to the antibody, which recognizes A antigen $(NeuGc)_2G_{D3}$. The 13G3 antibody recognizes the A antigen, which corresponds to the A antigen $(NeuGc)G_{T3}$ or a related antigen. These two antibodies can be used in combination to type feline blood. Any of a variety of different substrate kits or testing procedures can be used so long as these two antibodies or homologous antibodies thereof can be used to type the blood sample. Antibodies having receptor sites homologous to the glycolipid A antigen receptor sites discussed above can be used in the alternative to the antibodies labeled 13G3 and 4E10. Regardless, the antibody must accurately type feline blood group A samples.

The two antibodies could be used in any application that currently allows for the use of antibodies for typing blood. Additionally, the two antibodies can be used in future applications, including diagnostic use, research use, and therapeutic use. Such applications include, but are not limited to, red cell agglutination, microsphere agglutination, enzyme linked immunoassay, fluorescent antibody applications, immunoprecipitation, agar gel immunodiffusion, immunohistochemical applications, antibody-based antigen purification from tissues or fluids, and others. The antibodies could also have as-yet realized therapeutic applications.

The antibodies can be used alone or can be included as part of a kit. To prepare the kit it is preferred to obtain a card member having at least two wells. More preferably, the card member will contain enough wells for two controls and a sample to be tested. The additional wells are preferred to insure the accuracy of the results. Any of a variety of commercially available cards may be used so long as a monoclonal antibody mix can be readily placed on the card. An example of a preferred blood typing cardboard substrate card is a PATHODX® card, made by Diagnostic Products Corp., Los Angeles, Calif.

The above-discussed monoclonal antibodies can be optionally mixed into solution. The solution is preferably comprised of 0.02M phosphate-buffered saline with 2% bovine serum albumin (BSA). A blocking reagent such as STABILICOAT® (SurModics, Inc., Eden Prairie, Minn.) may be added at this stage, or can later be contacted with the mixture, as discussed below. The blocking reagent, such as STABILICOAT® is added to the antibody mixture to prevent degradation. Other solutions instead of the blocking reagent, STABILICOAT® may be used, as long as degradation of the antibodies is inhibited. Also, different amounts of PBS and BSA may be used.

Preferably the 13G3 monoclonal antibody is added to solution in an amount ranging between about 34 micrograms/milliliters (µg/ml) and about 136 µg/ml. More preferably the 13G3 antibody is added in an amount equal to about 68 µg/ml. The 4E10 is added to the solution in an amount ranging between about 64 µg/ml and about 256 µg/ml. More preferably, the 4E10 is added in an amount equal to about 128 µg/ml. Other amounts can be used; however, these amounts were observed to produce the best results. In fact, any amount can be used, as long as sufficient antibody is present to agglutinate the erythrocytes in the blood sample. Sufficient agglutination means that which is visible to the naked eye.

The antibody mixture, which is optionally in solution, is preferably mixed with an equal volume of plasma STABILICOAT®. The antibody mixture in solution with the blocking reagent, STABILICOAT® is then added to at least one well and more preferably three of the wells on the card member. The antibody and the blocking reagent, such as STABILICOAT® mixture is spread out over an entire defined area with a paintbrush. In other wells found on the substrate of the kit, an anti-B reagent, such as *Triticum vulgaris*, is added. Other anti-B reagents can be used in the alternative. Both the anti-B and anti-A reagents, after the antibodies have been mixed in solution with the blocking reagent, such as STABILICOAT®, are preferably added in an amount equal to between 50 microliters ($\mu$l) and 100 $\mu$l, although 100 $\mu$l is preferred. A combination that equals 100 $\mu$l may be used. The 100 $\mu$l amount is selected because it is an amount sufficient to allow for agglutination to be viewed by the naked eye. Other amounts, however, can be used.

The cards are preferably then frozen at $-20°$ C. for one hour followed by lyophilizing over night at $-10°$ C. Alternative methods that allow for long-term storage of a protein mixture may be used. The resultant cards can be stored at room temperature, but, they have an extended shelf life of greater than one year if they are stored at $4°$ C.

Alternatively, other substrate testing members can be used in place of the card. A test tube, or similar member that can house an antibody mixture may be used, for example. Any substrate device or system can be used that facilitates contact between the antibody mixture and the blood sample. Typically, the antibody mixture will be used in the same amount, regardless of the substrate.

A blood sample to be tested is taken from a feline subject. The blood sample can be comprised only of erythrocytes, or can contain plasma, serum, and other blood constituents. An anticoagulent, such as ethylene diaminetetracetic acid (EDTA), is added thereto. If a lyophilized card is used, 50 $\mu$l of PBS is added to each well to reconstitute the solution. Between 50 $\mu$l and 100 $\mu$l of the cat EDTA whole blood sample is added to an anti-A well and a sample is added to the anti-B well. Whole blood and PBS are mixed for 12 rotations, with the flattened end of a DISPENSTIR®, or wooden stick, to cover the entire oval. The card is rocked for 1 minute and read. If the blood agglutinates in the ovals with the anti-A monoclonal mixture, this indicates that the cat is blood type A. If the blood agglutinates with the anti-B reagent, it indicates blood type B. If the blood agglutinates with both anti-A and anti-B, it indicates blood type AB.

The present kit and method result in accurate identification of blood type in cats 99.9% of the time. Of course, correct procedures must be followed in order to insure accuracy. Also, alternatives to the card kit may be used. For instance, a test tube could be used instead of the card kit. Any type of kit variation may be used so long as the above listed antibodies are included.

The following examples are for illustrative purposes only and are not meant to limit the claims in any way.

EXAMPLES

Example 1

The following relates to a method for producing murine IgM monoclonal antibodies.

Feline blood samples were obtained from submissions to the Clinical Pathology Laboratory at Kansas State University and from a commercial veterinary laboratory (Colorado Veterinary Laboratories, Broomfield, Colo.). Blood used for screening of hybridomas and preparation of erythrocyte membranes was obtained from blood-typed A, B, and AB cats and six sheep maintained at the Kansas State University Animal Resources Facility. Sheep erythrocytes were used as a source of known membrane glycolipid profiles. Blood from the cats had been typed by a commercial laboratory (Stormont Laboratories, Woodland, Calif.) and by blood-typing cards in the laboratory. Samples were obtained by jugular venepuncture and submitted in EDTA anticoagulant.

Each blood sample was typed by tube agglutination or by using blood-typing cardboard substrate cards (PATHODX® cards, Diagnostic Products Corp., Los Angeles, Calif.). For typing on cards, 50 $\mu$l of whole blood was placed in various defined areas of the substrate member and mixed with 50 $\mu$l of either naturally occurring anti-A antiserum from a blood type B cat (undiluted) or WGL (60 $\mu$g/ml in phosphate buffered saline (PBS), pH 7.4). The card was rocked for 2 minutes and examined for macroscopic agglutination. For tube agglutination, 100 $\mu$l of anti-A antiserum or 100 $\mu$l of WGL (60 $\mu$l/ml diluted 1:8 in PBS (with 1% BSA) was added to 100 $\mu$l of a 1% saline suspension of erythrocytes. The contents of the tubes were mixed and incubated at room temperature for 15 minutes, then centrifuged and read for macroscopic agglutination.

Hemoglobin-free erythrocyte membrane ghosts were prepared within 24 hours of collection by hypotonic lysis (Dodge et al. 1962). If stored overnight, EDTA-anticoagulated samples were placed in acid citrate dextrose at $4°$ C. Either way whole blood was centrifuged at 3000 rpm for 10 minutes, plasma was removed, and packed erythrocytes were washed three times with 0.02 M PBS. Erythrocytes were lysed immediately with 10 mOsm sodium phosphate buffer containing 1 mOsm DIFP. Erythrocyte membranes were subsequently washed five or six times with 10 mOsm sodium phosphate buffer. The protein concentration of the erythrocyte membranes was measured by a bicinchoninic acid protein assay using bovine serum albumin standards. The membranes were then stored at $-70°$ C. until use.

Lipids were then extracted from the erythrocyte membranes using a modification of published procedures (Irwin and Irwin 1979). The membranes were mixed with 5 ml of chloroform:methanol (C:M) 2:1 (by volume) in tubes, which were then heated in a water bath at $60°$ C. for 5 minutes and centrifuged at 3000 rpm for 15 minutes to remove precipitated material. A supernatant containing the lipids was removed and dried under a stream of nitrogen. The dried lipids were resuspended in C:M 1:1 (by volume) for spotting on Thin-layer Chromatography (TLC) plates.

Thin-layer Chromatography was next used to isolate the A and B Antigens from the lipids. A 600 $\mu$l sample of erythrocyte membrane lipid extract was applied to preparative TLC plates in a horizontal band. Also, 40 $\mu$l of the same extract and 8 $\mu$l of the commercial standard $(NeuAc)_2 G_{D3}$ were applied in separate lanes to a perforated strip on the edge of the plate. The plate was developed in a glass chamber containing $C:M:2.5N\ NH_4OH$ (60:40:9, by volume). The filter paper was placed against the inside walls of the chamber with the bottom edges immersed in solvent to wick the solvent and maintain a saturated atmosphere within the chamber. The plate was developed until the solvent front was within 1 cm of the top of the plate. Following this, the plate was dried at room temperature. Glycolipid bands were visualized on the perforated strip by spraying with orcinol ferric chloride and heating to $100°$ C. Bands on the remaining (unstained) preparative plate were identified by comparison with those on the orcinol-stained companion strip. The corresponding desired region of the preparative plate was scraped off, placed into a 25 ml screw-top glass tube, and extracted twice by mixing with C:M 2:1 followed by centrifugation at 3000 rpm for 10 minutes, then extracted twice more using $C:M:H_2O$ (50:50:15, by volume). Supernatants from all extractions of each sample were pooled in a separate bell flask, and distilled to remove C:M. The remaining lipid residue was suspended in 1 ml of C:M 1:1. Purity of the isolated antigen was evaluated by TLC on aluminum-backed silica gel 60 High Performance Thin-layer Chromatography (HPTLC) plates and visualization with orcinol ferric chloride followed by heating to $100°$ C.

Liposomes incorporating the isolated erythrocyte membrane glycolipids were prepared using a modification of published procedures (Watarai et al. 1987). After combining 100 µl dipalmitoyl phosphatidylcholine (50 µmol/ml C:M 1:1), 20 µl *Salmonella Minnesota* lipopolysaccharide (5 mg/ml C:M 1:1), and 20 µl of the isolated erythrocyte membrane glycolipid, the organic solvent was evaporated under a nitrogen stream until the remaining lipids were completely dry. Lipids were resuspended in 5 ml of sterile PBS, heated at 50° C. in a water bath for 1 minute and sonicated for 1–3 seconds at 80% output (Ultrasonic Homogenizer, Cole-Parmer Instrument Co., Chicago, Ill.) until the suspension became cloudy. Female Balb/c mice were given a single intraperitoneal injection of 0.5 ml of liposome suspension in order to facilitate production of IgM antibodies for use in agglutination assays (Watarai et al. 1987).

The mice were euthanized 3 days after liposome immunization by inhalant anesthesia followed by cervical dislocation. Splenic lymphocytes were harvested, washed, and fused with AG8U.1 mouse myeloma cells (ATCC, Rockville, Md.) using 50% polyethylene glycol. Hybridomas were selected in 96-well plates containing Dulbecco's MEM supplemented with 12.5% heat-inactivated fetal calf serum L-glutamine, MEM non-essential amino acids, MEM vitamin solution, and gentamicin sulphate, with added hypoxanthine, aminopterin, and thymidine. Plates were incubated at 37° C. in 7.3% $CO_2$ for 10–14 days and screened when cell colonies were macroscopically visible.

Hybridoma culture supernatants were then screened for antibodies to feline type A or B erythrocytes. Erythrocytes from a blood type A cat or a blood type B cat were added to the 100 µl of hybridoma supernatant in each well. After incubation at room temperature for 15 minutes, tubes were centrifuged at 3000 rpm for 15 seconds and evaluated for macroscopic agglutination. Hybridomas exhibiting specific agglutination of type A or B feline erythrocytes were cloned by limiting dilution and expanded in non-selective media. Monoclonal antibody was produced in quantity by intraperitoneal injection of selected cloned hybridomas producing the desired antibody into pristane-primed Balb/c mice (Hoogenraad et al. 1983).

Monoclonal antibodies (MoAb) were isotyped using an antigen-specific isotyping system. Hybridoma supernatant from each MoAb (2:1 dilution in PBS-1% bovine serum albumen (BSA)-0.1% Tween 20) was incubated for 4 hours with two strips containing erythrocyte gangliosides separated by HPTLC. After washing, each strip was incubated for 1 hour with isotype specific reagents, either rabbit anti-mouse IgG1 or rabbit anti-mouse IgM (1:15 dilution in PBS-BSA-Tween 20), followed by a 1-hour incubation with goat anti-rabbit IgG horseradish peroxidase conjugate (1:4000 dilution in PBS-Tween 20). Strips were developed with substrate solution consisting of 400 µg/ml OPD in 80 mmol/l citrate-phosphate buffer pH 56.0, containing 0.03% $H_2O_2$.

Monoclonal antibodies were produced which could be tested for antigen specificity.

Example 2

The monoclonal antibodies of Example 1 were tested against a number of feline blood samples by tube agglutination. A 100 µl sample of hybridoma media from each MoAb was mixed with 100 µl of a 1% saline suspension of erythrocytes of each blood sample and incubated for 15 minutes at 37° C. The tubes were then centrifuged at 3000 rpm for 5 seconds and examined for agglutination. Agglutination reactions were graded on a scale of 0 to 4+, according to published procedures (Walker 1990).

Four IgM cell lines producing anti-A MoAbs (clones 13G3, 23G5, 4E10, 4G2) and two IgM cell lines producing anti-B MoAbs (clones 9D 10 and 17G7) were made. Agglutination test results of these MoAbs with erythrocytes from blood-typed cats are summarized in Table 1 below.

TABLE 1

| Monoclonal antibody | Number of samples agglutinated/total | | | Total number of samples tested |
|---|---|---|---|---|
| | Type A | Type B | Type AB | |
| 13G3 | 654/654 | 0/31 | 7/10 | 695 |
| 4G2 | 654/654 | 1/31 | 7/10 | 695 |
| 23G5 | 653/653 | 0/31 | 4/10 | 694 |
| 4E10 | 2074/2075 | 0/75 | 7/17 | 2167 |
| 9D10 | 3/1428 | 54/55 | 9/10 | 1493 |
| 17G7 | 3/1428 | 54/55 | 8/10 | 1493 |

Agglutination reactions with the MoAbs and feline typing reagents typically had a 3+ or 4+ score. All anti-A MoAbs except 4E10 agglutinated all blood type A samples. MoAb 4E10 did not detect 1 of 2075 blood type A samples; this sample was not tested with the other anti-A MoAbs but did not agglutinate when tested with the anti-B MoAbs. The anti-A MoAbs did not detect any blood type B samples, except MoAb 4G2, which agglutinated 1 of 31 type B samples at a 1+ agglutination score. All anti-A MoAbs were also tested against blood from 10 AB cats. MoAbs 13G3 and 4G2 each agglutinated the same 7 of 10 type AB samples. MoAbs 23G5 and 4E10 each agglutinated the same 4 of 10 type AB samples, which constituted a subset of the seven samples detected by MoAbs 13G3 and 4G2. The remaining three type AB samples were not agglutinated by any of the anti-A MoAbs, although they had agglutination scores of 3–4+ with feline blood-typing reagents. Each anti-A MoAb was also tested by rube agglutination with sheep erythrocytes. MoAbs 13G3 and 4G2 showed 2–3+ agglutination of erythrocytes from all sheep; MoAbs 4E10 and 23G5 did not agglutinate any sheep blood samples (data not shown). Erythrocyte membranes from one of these sheep were used for subsequent TLC immunostaining.

The anti-B MoAbs, 9D10 and 17G7, each detected 54 of 55 blood type B samples and 3 of 1428 type A samples. The one type B sample not detected by these MoAbs was different for each antibody. MoAb 17G7 strongly agglutinated the type B blood sample which did not agglutinate with 9D10, whereas MoAb 9D10 showed 1+ agglutination with the type B sample not detected by 17G7. Two of the three type A samples erroneously detected were the same for both anti-B MoAbs. One of these blood samples agglutinated at only a trace to 1+ with each anti-B MoAb; the second blood sample was haemolysed by MoAb 9D10, agglutinated at 2+ by 17G7, and reacted atypically with feline typing reagents (agglutinating at only 1+ with anti-B MoAb) each agglutinated at 2+. Monoclonal antibody 9D10 detected 9 of 10, and MoAb 17G7 detected 8 of 10 type AB samples (Table 1).

It was determined that monoclonal antibodies accurately typed feline blood samples. The primary application for which antibodies were developed and selected is feline red blood cell typing by direct red blood cell agglutination procedure.

Example 3

The following example was performed to show antigen specificity of the monoclonal antibodies of the present invention.

About 25–35 µl of glycolipid extract was applied to each lane of HPTLC plates. The ganglioside standard (NeuAc) $_2G_{D3}$, was prepared by reconstitution in 1 ml C:M 1:1, and 6–8 µl was applied per lane. Plates were developed in C:M:NH$_4$OH solvent (60:40:9 by volume) as described previously. One strip was treated with orcinol and heated at 100° C. for visualization of glycolipid bands; the remaining strips were immunostained using a modification of published procedures (Buehler and Macher 1986). After drying, the strips were plastic-coated uniformly with 0.3% poly (isobutylmethacrylate) in hexane and air dried. Strips were blocked for 1 hour in PBS-1% BSA-0.1% Tween 20, washed three times with PBS-Tween 20, and incubated for 4 hours with anti-A or anti-B MoAb hybridoma supernatant (2:1 dilution), MoAb 32-27 (1:20 dilution), or MoAb R-24 (10 µg/ml). Strips were washed three times in PBS-Tween 20 and incubated in biotinylated goat anti-human IgM or biotinylated goat anti-mouse IgM. All MoAbs and biotinylated antibodies were diluted in PBS-BSA-Tween 20. Strips were washed three times in PBS-Tween 20, incubated with ABC reagent in PBS-Tween 20 for 1 hour, and washed again three times with PBS. Strips were developed in substrate solution consisting of 400 µl/ml OPD in 80 mmol/l citrate phosphate buffer, pH 5.0, containing 0.03% H$_2$O$_2$.

The binding specificity of the anti-A MoAbs was evaluated by TLC immunostaining of erythrocyte membrane glycolipids from a type A cat, a type B cat or a commercial (NeuAc)$_2$G$_{D3}$ standard, and a sheep, in comparison with human MoAb 32-27 (anti-(NeuGc)$_2$G$_{D3}$). MoAbs 23G5 and 4E10 each stained a common band in type A samples which comigrated with (NeuGc)$_2$G$_{D3}$. MoAbs 13G3 and 4G2 also detected an identical single band in type A glycolipids which migrated slightly behind (NeuGc)$_2$G$_{D3}$. MoAb 32-27 strongly stained three bands in the type A sample, the largest of which comigrated with (NeuGc)$_2$G$_{D3}$ and another of which comigrated with the band detected by MoAbs 13G3 and 4G2. The bands detected in the sheep glycolipids by MoAb 32-27 were different from those detected in the type A sample. None of the four anti-A MoAbs detected bands from either type B glycolipids or a commercial (NeuAc)$_2$G$_{D3}$ standard. Similarly, MoAb 32-27 did not react with type B glycolipids. TLC immunostaining of erythrocyte membrane glycolipids from 38 additional type A cats was done with MoAbs 4E10 and 13G3. In all 38 cats, 4E10 detected a band.

The TLC immunostaining characterization of the anti-B MoAbs was done with erythrocyte membrane glycolipids from the same blood type A and B cats. Both MoAbs 9D10 and 17G7 recognized the same band in blood type B glycolipids which comigrated with the commercial (NeuAc)$_2$G$_{D3}$ standard as visualized by orcinol staining. The murine MoAb R-24 (anti-(NeuAc)$_2$G$_{D3}$) detected a band at the same position in type B samples. Neither anti-B MoAb nor MoAb R-24 detected bands from type A glycolipids.

The accuracy of the monoclonal antibodies in typing feline blood type A was further verified.

Example 4

Erythrocyte membrane proteins were separated on polyacrylamide slab gels (7.5%) containing SDS Sodium dodecyl Sulphate Polyacrylaminde Gel Electrophoresis (SDS-PAGE)/Immunoblotting) using a discontinuous buffer system. Biotinylated high molecular-weight standards were used for reference. Separated proteins were transferred electrophoretically to a PVDF membrane, which was then washed for 20 minutes with PBS. Blots were blocked in PBS, with 0.2% BSA overnight at 4° C., followed by three washes with PBS-0.05% Tween 20. Blots were incubated with anti-A or anti-B MoAbs diluted 2:1 with PBS-BSA-Tween 20 for 4 hours at 37° C., washed, and then incubated for 1 hour with biotinylated goat anti-mouse IgG or IgM (1:200 dilution in PBS-BSA-Tween 20). Blots were washed three times in PBS-Tween 20 and incubated for 1 hour with ABC reagent. After final washes in PBS-Tween 20 and PBS, blots were developed with 4-CN-DAB (4-chloronaphtholdiaminobenzidine (Pierce Chemical Co., Rockford, Ill.)) substrate according to the manufacturer's directions.

Immunoblotting of SDS-PAGE preparations of erythrocyte membrane proteins from the above blood type A and B cats was conducted for each anti-A and anti-B MoAb (data not shown). Though slight differences in banding patterns were seen between antibodies, no differences were present between glycoproteins of type A and B cats for any antibody. In both A and B samples, all six MoAbs detected a band at approximately 74 kDa, and MoAb 4G2 detected an additional band at 45 kDa. A negative control (hybridoma media) did not stain any band in either type A or B erythrocyte membrane proteins.

Example 5

The following test was conducted to determine the correct amount of each antibody to be used with the test. A card agglutination test was performed. Whole blood was used. The specific antibodies and concentrations tested are listed in Table 2, below. To test agglutination, the antibodies were diluted in PBS with 2% of BSA to the desired dilution listed below. The antibody mixture was placed in wells on a rectangular card. 50 µl samples of the antibodies were then mixed with 50 µl samples of whole blood. Agglutination reactions were graded on a scale of 0 to 4+, according to published procedures (Walker 1990). The card test was conducted to determine the correct amount of antibodies. The card test is less sensitive than the tube agglutination test.

TABLE 2

| Cat Name and Blood Type | 4E10 dil × 10 320 µg/ml | 13G3 dil × 25 168 µg/ml | Mixed 4E10 and 13G3 1:1 Equal Volume of Each Diluted Antibody | | |
|---|---|---|---|---|---|
| | | | 13G3 × 25 4E10 × 10 | 13G3 × 50 4E10 × 20 | 13G3 × 100 4E10 × 40 |
| Jasmine (AB) | = | 4+ | 4+ | 4+ | 4+ |
| Abbie (AB) | 1+ | 4+ | 4+ | 4+ | 4+ |
| DJ (AB) | = | 4+ | 4+ | 4+ | 4+ |
| Molly (AB) | = | 4+ | 4+ | 4+ | 4+ |
| Simon (A) | 4+ | 4+ | 4+ | 4+ | 4+ |
| Ash (A) | 4+ | 4+ | 4+ | 4+ | 4+ |
| BVD (A) | 4+ | 4+ | 4+ | 4+ | 4+ |
| Houdini (B) | = | = | = | | |

The following is a list of the dilutions recited in Table 2:

4E10 at 3.2 mg/ml=3,200 µg/ml
    diluted×10=320 µg/ml diluted×20=160 μg/ml
diluted×40=80 μg/ml
13G3 at 4.2 mg/ml=4,200 μg/ml
diluted×25=168 μg/ml
diluted×50=84 μg/ml
diluted×100=42 μg/ml As can be seen in Table 2, the 4E10 at 320 μg/ml was not present in a sufficient amount to cause adequate agglutination with an AB blood type. 4E10 at 320 μg/ml was sufficient to agglutinate with the A blood type. The 13G3 at 168 μg/ml was present in a sufficient amount to cause adequate agglutination with both the AB and A blood types. The mixture of the two antibodies combined caused adequate agglutination with both the AB and A blood types.

Example 6

The procedures of Example 5 were performed using different amounts of individual and combined antibodies.
4E10 at 3.2 mg/ml=3,200 μg/ml
diluted×10=320 μg/ml
13G3 at 4.2 mg/ml=4,200 μg/ml
diluted×25=168 μg/ml
diluted×50=84 μg/ml
diluted×100=42 μg/ml
diluted×200=21 μg/ml
diluted×400=10.5 μg/ml
diluted×800=5.25 μg/ml The results appear in Table 3, below.

50 μl antibody diluted in PBS with 2% BSA, was mixed with 50 μl whole blood.

TABLE 3

| Cat | 4E10 dil × 10 | 13G3 dil × 200 | Mixed 13G3 × 200 plus 4E10 × 10 |
|---|---|---|---|
| 1 A cat | 4+ | 4+ | 4+ |
| 2 A cat | 4+ | 4+ | 4+ |
| 3 A cat | 4+ | 4+ | 4+ |
| 4 A cat | 4+ | 4+ | 4+ |
| 5 A cat | 4+ | 4+ | |
| 6 A cat | 4+ | 4+ | |
| 7 A cat | 4+ | 4+ | |
| 8 A cat | 4+ | 4+ | |
| 9 A cat | 4+ | 4+ | |

Table 4 shows that the 13G3 antibody can be significantly diluted before agglutination is impacted. An amount of 13G3 antibody equal to 21 μg/ml (13G3 diluted×200) caused adequate agglutination. Also, 4E10, alone, did not readily agglutinate with the AB blood type, but did agglutinate with blood type A.

Example 7

A feline blood typing card was prepared as follows:
Two anti-A monoclonal antibodies, 13G3 and 4E10, produced according to the method of Example 1, were mixed in 0.02 M Phosphate buffered saline (PBS) with 2% bovine serum albumin. The concentration of murine IGM monoclonal antibodies 13G3 and 4E10 were, respectively, 68 μg/ml and 128 μg/ml. An equal volume of a blocking reagent, STABILICOAT® Immunoassay Stabilizer (SurModics, Inc. 9924 West 74th Street, Eden Prairie, Min. 55344-3523) was added to the monoclonal antibody mixture. The blood typing card had eight wells. 100 μl of the monoclonal antibody mixture was placed inside each of four wells and spread over the wells with a #5 paintbrush.

The "Anti-B reagent" was a lectin from *Triticum vulgaris* (wheat germ), with 1% DMSO, and 0.0036 g/ml glucose. The lectin (6 mg) was dissolved in 100 ml of phosphate buffered saline. 100 μl of the lectin was placed inside each of the remaining four wells and spread over the wells with a #5 paintbrush.

The card was frozen at −20° C. for one hour, and then lyophilized at −10° C. The card was sealed in polytubing with one dessicant pack. The card was stored at 4° C. and was ready for use.

Example 8

The procedures of Example 7 were followed with the test cards of the present Example. The test cards had an amount of antibody equal to:
13G3 diluted×200 (4.3 mg/ml) 22 μg/ml=55 μl+10 ml
4E10 diluted×10 (3.2 mg/ml) 320 μg/ml=1 ml+9 ml The cards were designed to test more than one cat. 50 μl of whole blood taken from 1 of 14 cats was then placed on a test card to determine the cat's blood type. Prior to adding the blood sample, 50 μl of PBS was added to the test wells to reconstitute the antibody solution. A total of 14 test samples were run. The results for an AB blood type cat were:
50 μl Abbie AB cat whole blood with
13G3 at 22 μg/ml—pos
4E10 at 320 μg/ml—pos
13G3 plus 4E10 mixed (11 μg/ml 13G3 and 160 μg/ml 4E10)—pos The results are shown in Table 4. As seen in Table 4, the 13G3/4E10 antibody mixture successfully identified all of the cats having an A blood type. The 13G3/4E10 antibody mixture also successfully identified three out of four AB blood type cats. Only Molly AB cat showed up as negative for A.

TABLE 4

| Cat | 4E10 dil × 10 | 13G3 dil × 25 | 13G3 dil × 50 | 13G3 dil × 100 | 13G3 dil × 200 | 13G3 dil × 400 | 13G3 dil × 800 | Mixed 13G3 × 200 plus 4E10 × 10 |
|---|---|---|---|---|---|---|---|---|
| D.J. AB | = | 4+ | 4+ | 4+ | 4+ | 4+ | 3+ | 4+ |
| Molly AB | = | 4+ | 4+ | 4+ | 4+ | 3+ | 2+ | 3+ |

TABLE 4

| Cat | α A (13G3) (4E10) | α B (WGL) |
|---|---|---|
| 1 A Cat | Positive | Negative |
| 2 A Cat | Positive | Negative |
| 3 A Cat | Positive | Negative |
| 4 A Cat | Positive | Negative |
| 5 A Cat | Positive | Negative |

TABLE 4-continued

| Cat | α A (13G3) (4E10) | α B (WGL) |
|---|---|---|
| 6 A Cat | Positive | Negative |
| 7 A Cat | Positive | Negative |
| 8 A Cat | Positive | Negative |
| 9 A Cat | Positive | Negative |
| 10 A Cat | Positive | Negative |
| D.J. AB | Positive | Positive |
| Molly AB | Negative | Positive |
| Abbie AB | Positive | Positive |
| Houdini AB | Positive | Positive |

Molly AB cat was repeated with only 25 μl of whole blood on the test card. This resulted in a positive reading for A.

TABLE 5

| Molly | α A | α B |
|---|---|---|
| 25 μl | Positive | Positive |
| 10 μl | Positive | Positive |
| B Cat 25 μl | Negative | Positive |

Molly AB cat was also repeated with only 10 μl of whole blood (1 drop PBS, plus 1 drop whole blood) and mixed with 1 drop from×2 dilution. These results appear in Table 5.

As can be seen from Tables 4 and 5, the combination of antibodies readily types A and AB blood types.

Example 9

The procedure of Example 5 was followed. The results appear in Table 6.

13G3 1.7 mg/ml diluted×25=68 μg/ml
4E10 3.2 mg/ml diluted×25=128 μg/ml

TABLE 6

| | 13G3 × 25 | 4E10 × 50 | 4E10 × 25 | 4E10 × 25 13G3 × 25 | 4E10 × 25 13G3 × 25 Plus 1:1 StabiliCoat ® |
|---|---|---|---|---|---|
| Jasmine AB | 4+ | Negative | Negative | 4+ | 4+ |
| Abbie AB | 4+ | 1+ | 3+ | 4+ | 4+ |

The 4E10 antibody, alone, did not result in agglutination with the AB blood type. The mixture of 4E10 and 13G3 did result in clear identification of the AB blood type.

Example 10

Blood typing cards using the antibodies of Example 1 and the procedure of Example 7 were tested to evaluate for accuracy in comparison to the standard methods described above. Again, a mixture of the two monoclonal antibodies were used to detect blood type A. The typing cards correctly identified 225 of 225 type A samples, did not detect any type B samples (0 of 16 tested), and identified 5 of 5 type AB samples.

It was determined that monoclonal antibodies used in the card test accurately typed feline blood samples. The primary application for which antibodies were developed and selected is feline red cell typing by direct red cell agglutination procedure.

Thus, there has been shown and described a method and kit for typing feline blood type, which fulfills all the objects and advantages sought therefore. It is apparent to those skilled in the art, however, that many changes, variations, modifications, and other uses and applications for the method and kit for typing feline blood type are possible, and also such changes, variations, modifications, and other uses and applications which do not depart from the spirit and scope of the invention are deemed to be covered by the invention, which is limited only by the claims which follow.

REFERENCES

Buehler J, Macher B A (1989) Glycosphingolipid immunostaining: detection of antibody binding with an avidin-biotin enzyme system. Anal Biochem 158:283–287

Dodge J. Mitchel C, Hanahan D (1962) The preparation and chemical characteristics of hemoglobin-free ghosts of human erythrocytes. Arch Biochem Biophys 100:119–130

Hoogenraad N, Helman T, Hoogenraad J (1983) The effect of pre-injection of mice with pristane on ascites formation and monoclonal antibody production. J Immunol Meth 61:317–320

Irwin C C, Irwin L N (1979) A simple rapid method for ganglioside isolation from small amounts of tissue. Anal Biochem 94:333–339

Walker R H (ed) (1990) In: Technical manual. American Association of Blood Banks, Arlington, Va., pp 528–529

Watarai S, Handa S, Tadakuma T et al. (1987) Application of liposomes to generation of monoclonal antibody to glycosphingolipid: production of monoclonal antibody to GgOsedCer. J Biochem 102:59–67

Comparative Haemotology (1991) 1:196–199

Blood. Vol. 79 No. 9 (May 1992), pp 2485–2491

Comparative Haematology (1991) 1:217–219

What is claimed is:

1. A kit for determining feline blood type, comprising:
   (a) a substrate which allows contact between at least one monoclonal antibody and a feline blood sample; and,
   (b) a mixture of a first monoclonal antibody and a second monoclonal antibody placed in contact with said substrate, whereby each said antibody recognizes at least one feline blood group specific A antigen.

2. The kit of claim 1 wherein said first or said second monoclonal antibody in said mixture recognizes glycolipid A antigen (NeuGc)$_2$G$_{D3}$.

3. The kit of claim 1 wherein said first or said second monoclonal antibody in said mixture recognizes glycolipid A antigen comprising (NeuGc)G$_{T3}$, or (NeuGc) containing gangliosides.

4. The kit of claim 3 wherein said monoclonal antibody is present in solution at a concentration equal to between 34 μg/ml and 136 μg/ml.

5. The kit of claim 2 wherein said monoclonal antibody is present in solution at a concentration equal to between 64 μg/ml and 256 μg/ml.

6. The kit of claim 1 wherein said antibody mixture has been lyophilized.

7. The kit of claim 1 wherein said substrate is selected from the group consisting of cards and test tubes.

8. The kit of claim 1 wherein said kit comprises an agent which agglutinates with blood type B.

9. The kit of claim 8 wherein said agent is a lectin from *Triticum vulgaris*.

10. A method for typing feline blood samples comprising:
(a) collecting a blood sample from a feline subject;
(b) dispensing an amount of the blood sample into a substrate, which includes a mixture of a first monoclonal antibody and a second monoclonal antibody, each said antibody agglutinates feline blood group A specific antigens; and,
(c) examining the blood sample and antibody mixture to determine whether the sample agglutinated.

11. The method of claim 10 wherein between 50 $\mu$l and 100 $\mu$l of the blood sample, which is collected in ethylene diaminetetracetic acid, from the feline subject to be typed, is added to said substrate.

12. The method of claim 10 wherein said first or said second monoclonal antibody in said mixture recognizes glycolipid A antigen $(NeuGc)_2G_{D3}$.

13. The method of claim 10 wherein said first or second monoclonal antibody, which recognizes glycolopid A antigen $(NeuGc)_2G_{D3}$ is present in a concentration equal to between 64 $\mu$g/ml and 256 $\mu$g/ml.

14. The method of claim 10 wherein said blood sample is mixed with said antibody mixture in an amount wherein agglutination can be observed.

15. A method of using monoclonal antibodies to type feline blood, comprising: contacting a sample of feline blood with a mixture of murine monoclonal antibodies wherein at least one of said antibodies agglutinates glycolipid A antigen $(NeuGc)_2G_{D3}$, and at least one of said antibodies agglutinates glycolipid A antigen $(NeuGc)G_{T3}$, or (NeuGc) containing gangliosides and determining feline blood type based on agglutination or the absence of agglutination.

16. A kit for determining feline blood type, comprising a substrate including a monoclonal antibody mixture comprised of a first monoclonal antibody which recognizes glycolipid A antigen $(NeuGc)_2G_{D3}$, and a second monoclonal antibody which recognizes glycolipid A antigen $(NeuGc)G_{T3}$, or (NeuGc) containing gangliosides, whereby said first antibody is present in a concentration equal to between 64 $\mu$g/ml and 256 $\mu$l/ml, and said second antibody is present in a concentration equal to between 34 $\mu$g/ml and 136 $\mu$g/ml.

17. The method of claim 10 wherein said first or said second monoclonal antibody in said mixture recognizes glycolipid A antigen $(NeuGc)G_{T3}$.

18. The method of claim 17 wherein said first or second monoclonal antibody, which recognizes glycolopid A antigen $(NeuGc)G_{T3}$ is present in a concentration equal to between 34 $\mu$g/ml and 136 $\mu$g/ml.

* * * * *

UNITED STATES PATENT AND TRADEMARK OFFICE
CERTIFICATE OF CORRECTION

PATENT NO. : 6,830,895 B2
DATED : December 14, 2004
INVENTOR(S) : Gordon A. Andrews et al.

It is certified that error appears in the above-identified patent and that said Letters Patent is hereby corrected as shown below:

Column 12,
Line 59, delete "Table 4" and insert -- Table 5 -- therefor

Column 13,
Line 2, delete "Table 4-continued" and insert -- Table 5 - continued -- therefor
Lines 18 and 27, delete "Table 5" and insert -- Table 6 -- therefor
Line 28, delete "Tables 4 and 5" and insert -- Tables 5 and 6 -- therefor
Lines 33 and 37, delete "Table 6" and insert -- Table 7 -- therefor Signed and Sealed this Tenth Day of May, 2005

JON W. DUDAS
*Director of the United States Patent and Trademark Office*